United States Patent [19]

Jasserand et al.

[11] Patent Number: 6,001,833

[45] Date of Patent: Dec. 14, 1999

[54] UREA DERIVATIVES

[75] Inventors: Daniel Jasserand; Samuel David, both of Hannover; Jochen Antel, Bad Muender; Reinhard Brueckner, Hannover; Christian Eeckhout, Lindwedel; Gerhard-Wilhelm Bielenberg, Alfeld, all of Germany

[73] Assignee: Solvay Pharmaceuticals GmbH, Hannover, Germany

[21] Appl. No.: 09/141,623

[22] Filed: Aug. 27, 1998

[30] Foreign Application Priority Data

Aug. 27, 1997 [DE] Germany ............................ 197 37 274

[51] Int. Cl.$^6$ ........................ A61K 31/47; C07D 403/06
[52] U.S. Cl. ............................... 514/253; 544/373
[58] Field of Search ............... 544/373; 514/253

[56] References Cited

FOREIGN PATENT DOCUMENTS

| | | |
|---|---|---|
| 655442 | 5/1995 | European Pat. Off. . |
| 832887 | 4/1998 | European Pat. Off. . |
| WO 96/37489 | 11/1996 | WIPO . |
| WO 97/11069 | 3/1997 | WIPO . |
| WO 97/28141 | 8/1997 | WIPO . |

*Primary Examiner*—Emily Bernhardt
*Attorney, Agent, or Firm*—Evenson, McKeown, Edwards & Lenahan, P.L.L.C.

[57] ABSTRACT

Compounds of Formula I

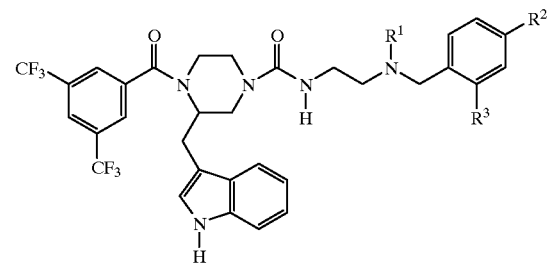

wherein $R^1$ is hydrogen or lower alkyl, $R^2$ is hydrogen or halogen and $R^3$ is hydrogen or lower alkoxy, and their pharmacologically acceptable acid addition salts and pharmaceutical compositions containing these compounds and also processes for the preparation of these compounds. Pharmaceutical composition containing these compounds are suitable, for example, for treating functional and inflammatory disorders of the gastrointestinal tract.

5 Claims, No Drawings

UREA DERIVATIVES

FIELD OF THE INVENTION

This invention relates to novel urea derivatives in which one nitrogen atom forms part of a piperazine ring and the other is substituted by a benzylaminoethyl group. These novel urea derivatives are distinguished by properties antagonistic to neurokinin receptors with an activity profile beneficial for the treatment of functional and inflammatory disorders of the gastrointestinal tract of larger mammals, in particular humans. The invention also relates to pharmaceutical compositions containing these novel compounds and to processes for preparing such compounds.

Piperazine derivatives having properties antagonistic to neurokinin receptors are already known from U.S. Pat. No. 5,670,505 (=EP 655,442).

SUMMARY OF THE INVENTION

It is an object of the invention to provide new active substances for treating functional and inflammatory disorders in the gastrointestinal tract.

It has now been discovered that a group of novel piperazine derivatives which are substituted in the 2-position by an indolylmethyl radical and in which the nitrogen in the 4-position of the piperazine ring forms part of a urea structure bearing a benzylaminoethyl substituent have an activity profile which makes them suitable for the treatment of functional and inflammatory disorders of the gastrointestinal tract. The group of substances according to the invention is furthermore characterized by good compatibility and good oral bioavailability.

The invention therefore relates to novel compounds of formula I

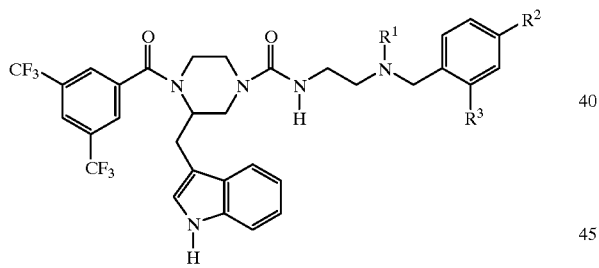

wherein
$R^1$ is hydrogen or lower alkyl,
$R^2$ is hydrogen or halogen and
$R^3$ is hydrogen or lower alkoxy,
and their physiologically acceptable acid addition salts, and also to medicaments or pharmaceutical compositions which can be produced from these compounds.

If in the compounds of Formula I the substituents represent or contain lower alkyl, this may be straight-chain or branched, and contain 1 to 4, preferably 1 or 2, carbon atoms. If $R^1$ stands for lower alkyl, methyl is preferred. If the substituent $R^2$ is halogen, fluorine is preferred. If the substituent $R^3$ is lower alkoxy, methoxy is preferred.

Compounds of Formula I in which $R^2$ stands for hydrogen and $R^3$ stands for methoxy, or compounds of Formula I in which $R^2$ is fluoride and $R^3$ stands for hydrogen, are preferred.

The 1H-indol-3-yl-methyl group is preferably located in the 2R position of the piperazine ring.

The compounds can be prepared using known techniques. Particularly beneficially, the compounds of Formula I can be prepared by a) reacting the compound of Formula II

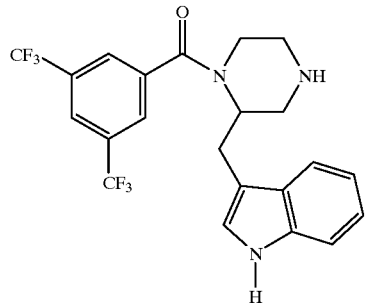

with a reactive carbonyl compound of the general formula III,

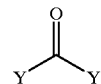

wherein Y represents a leaving group which can be displaced by nucleophilic attack of a primary or secondary amine, to form a carbamoyl compound of the general formula IV,

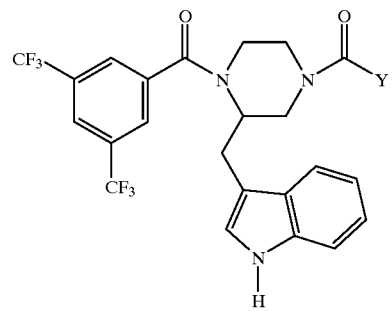

wherein Y has the above meaning, provided that by cleaving off the leaving group Y from a resulting compound of Formula IV an acid can be produced, adding a non-nucleophilic organic base to the compound of Formula IV, and by then reacting the compound of Formula IV with a compound of the general formula V,

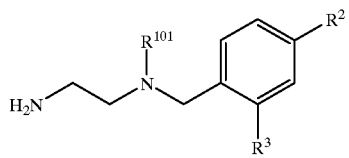

wherein $R^{101}$ represents lower alkyl or an amino protective group and $R^2$ and $R^3$ have the above meanings, and then cleaving off any protective group $R^{101}$ again, or by b) reacting the compound of Formula II with a compound of the general formula VI,

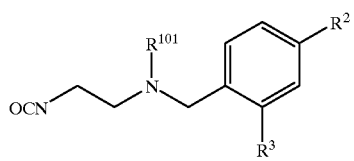

wherein $R^{101}$, $R^2$ and $R^3$ have the above meanings, and subsequently cleaving off any amino protective group $R^{101}$ again,
and optionally alkylating resulting compounds of Formula I wherein $R^1$ is hydrogen to form compounds of Formula I wherein $R^1$ is lower alkyl, and/or optionally converting resulting compounds of Formula I into their acid addition salts or optionally converting acid addition salts into free compounds of Formula I.

Advantageously, in accordance with process variant a) a compound of Formula II initially can be reacted with a reactive carbonyl compound of Formula III to form a carbamoyl compound of Formula IV, which can be reacted directly in situ, optionally after the addition of a non-nucleophilic organic base, with an amine of Formula V. Suitable leaving groups Y in compounds of Formula III include, for example, halogens, preferably chlorine, trihalomethoxy groups, preferably trichloromethoxy groups, or alternatively imidazolyl groups. Preferably, phosgene, bis-(trichloromethyl)-carbonate (triphosgene), trichloromethyl chloroformate (diphosgene) or carbonyl diimidazole can be used as reactive carbonyl compounds of Formula III. Upon the reaction of an amine of Formula V with a carbamoyl compound of Formula IV, the leaving group Y is displaced from the compound of Formula IV. Provided that an acid can be produced from the group Y which is released thereby, advantageously a non-nucleophilic organic base can be added to the compound of Formula IV before the reaction with the compound of Formula V. If Y stands, for example, for chlorine, the hydrochloric acid produced upon the cleaving-off of Y can be captured by adding an above-named base. Suitable non-nucleophilic bases are organic bases which are soluble in the reaction mixture, such as tertiary nitrogen bases, for example nitrogen-containing N-alkylated heterocycles such as N-lower alkyl morpholine or N-lower alkyl piperidine or tertiary lower alkylamines and pyridines, such as triethylamine, tripropylamine, diisopropylethylamine, pyridine, 4-dimethylaminopyridine, 4-diethylaminopyridine or 4-pyrrolidinopyridine. Bases used in excess may also serve as solvents. The reaction sequence can be carried out as a one-pot reaction in a polar aprotic solvent such as a partially halogenated lower hydrocarbon, for example dichloromethane, at temperatures between −20° C. and room temperature, preferably at room temperature.

The reaction of the compound of Formula II with an isocyanate of Formula VI in accordance with process variant b) may be effected in a known manner. The compounds of Formula VI may, for example, be obtained from the amines of Formula V by reaction with suitable reactive carbonyl compounds. Suitable reactive carbonyl compounds include, for example, the compounds of Formula III. Advantageously, an isocyanate of Formula VI first is prepared from an amine of Formula V, and this is then reacted directly in situ with a compound of Formula II. The reaction sequence can be performed as a one-pot reaction under the conditions stated above for the preparation of compounds of Formula I according to process variant a). Advantageously, an acid-binding reagent may be added to the reaction mixture. Suitable acid-binding reagents include the non-nucleophilic bases stated above.

Suitable amino protective groups $R^{101}$ include amino protective groups which are known, for example, from peptide chemistry, which can be introduced and cleaved off again using known methods. Suitable protective groups are disclosed, for example, in J. A. W. McOmie, "Protective Groups in Organic Chemistry", Plenum Press 1973, or T. W. Green and P. G. M. Wuts "Protective Groups in Organic Synthesis", Wiley and Sons 1991.

For example, groups which are largely stable in acid and in alkaline medium and which can be cleaved off under hydrogenolytic conditions are suitable as amino protective groups $R^{101}$. These include, for example, phenyl lower alkyloxy carbonyl groups such as the benzyloxy carbonyl group (abbreviated to CbO below). Preferably the benzyloxy carbonyl group, which can be cleaved in known manner, e.g. by catalytic hydrogenation, in order to obtain compounds of Formula I in which $R^1$ is hydrogen, can be used as amino protective group $R^{101}$. The cleaving of the protective group can be effected in an organic solvent which is inert under the reaction conditions, such as a lower aliphatic ether, for example tetrahydrofuran (abbreviated to THF below) or diethyl ether, lower alkanols, for example methanol or ethanol, or organic acids, for example lower aliphatic carboxylic acids such as acetic acid, or in mixtures of these solvents and in the presence of a hydrogenation catalyst. Suitable hydrogenation catalysts include, for example, precious metal catalysts such as palladium on activated carbon. Advantageously, the reaction is carried out at room temperature. A suitable hydrogen pressure for hydrogenation is between 2 and 7 bar, preferably between 3 and 5 bar.

If desired, compounds of Formula I in which $R^1$ is hydrogen may be converted according to known methods for aminoalkylation into compounds of Formula I in which $R^1$ is lower alkyl. For this, the compounds of Formula I may for example be reductively alkylated by reaction with lower aliphatic aldehydes such as formaldehyde. The reaction can be performed under conventional conditions for the reductive alkylation of amines, for example under the conditions of catalytic hydrogenation. Suitable hydrogenation catalysts include metal catalysts such as Raney nickel. Preferably lower alkanols can be used as solvents. The catalytic hydrogenation can be performed under the conditions described above for the hydrogenolytic cleaving of amino protective groups $R^{101}$.

Another possible method of alkylation is the reaction of compounds of Formula I in which $R^1$ is hydrogen with lower aliphatic alkyl halides such as alkyl bromides or alkyl iodides, preferably methyl iodide, alkyl sulfates or alkylsulfonic acid esters, under conditions generally usable for nucleophilic substitution reactions. The reaction can be performed in a polar aprotic solvent such as dimethyl formamide (abbreviated to DMF below), dimethyl sulfoxide (abbreviated to DMSO below) or acetonitrile at temperatures between −20° C. and 100° C., preferably between 60° C. and 90° C., and using an acid-binding reagent. Suitable acid-binding reagents include, for example, the organic bases given above for the reaction of the compounds of Formula IV with the compounds of Formula V.

Physiologically acceptable salts of compounds of Formula I are their salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or benzenesulfonic acids optionally substituted in the benzene ring by halogen or lower alkyl, such as p-toluenesulfonic acid.

The compounds of Formula I can be isolated from the reaction mixture and purified in known manner. Acid addition salts can be converted into the free bases in conventional manner, and these may if desired be converted in known manner into pharmacologically acceptable acid addition salts.

The compounds of Formula I contain an assymetric or chiral carbon atom, namely the carbon atom bearing the 1H-indol-3-ylmethyl group in the 2-position of the piperazine parent structure. The compounds of Formula I thus may exist in several stereoisomeric forms. The present invention includes both the mixtures of optical isomers and the isomerically pure compounds of Formula I. Compounds of Formula I in which the indolylmethyl group is located in the 2R position of the piperazine ring are preferred.

If mixtures of optical isomers of the starting compound of Formula II are used in the synthesis of the compounds of Formula I, the compounds of Formula I are also obtained in the form of mixtures of optical isomers. Starting from stereochemically uniform forms of the starting compound, it is also possible to obtain stereochemically uniform compounds of Formula I. The stereochemically uniform compounds of Formula I can be obtained from the mixtures of optical isomers in known manner, for example by chromatographic separation on chiral separating materials or by reaction with suitable optically active acids, for example tartaric acid or 20-camphorsulfonic acid, and subsequent separation into the optically active antipodes by fractional crystallisation of the resulting diasteereomeric salts.

The two possible enantiomers of the compound of Formula II are known from EP-A-655 422, and can be prepared according to the processes described in this patent application or analogously to these processes.

The amines of Formula V can be obtained from the doubly amino-protected diamino compounds of the general formula VII,

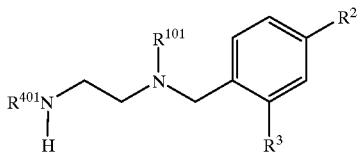

wherein $R^{101}$, $R^2$ and $R^3$ have the above meanings and $R^{401}$ stands for an amino protective group, by selectively cleaving off the amino protective group $R^{401}$ from compounds of Formula VII in known manner.

Amino protective groups which are generally known, for example from peptide chemistry, such as are known from the sources given above, are suitable as amino protective groups $R^{401}$. For example, groups which can be cleaved selectively and which are largely stable against hydrogenolytic and alkaline conditions are suitable as amino protective groups $R^{401}$ in at least moderately acidic medium, for example due to the addition of p-toluenesulfonic acid, trifluoroacetic acid or gaseous hydrochloric acid or hydrochloric acid dissolved in solvents. These include, for example, branched lower alkyloxy carbonyl groups such as the tert. butyloxycarbonyl group (abbreviated to BOC below). Preferably $R^{401}$ may stand for the tert. butyloxycarbonyl group.

Compounds of Formula VII can be obtained in known manner, for example by reduction of amides of the general Formula VIII,

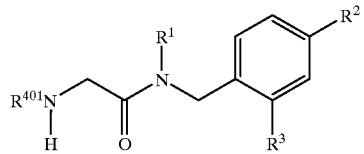

wherein $R^1$, $R^2$, $R^3$ and $R^{401}$ have the above meanings, and, if $R^1$ stands for hydrogen, subsequent introduction of a protective group $R^{101}$. The reduction can be effected with complex alkali metal hydrides such as lithium aluminium hydride as reduction agent. Suitable solvents include organic solvents which are inert under the reaction conditions, such as lower aliphatic ethers, for example dioxane, tetrahydrofuran (THF) or diethyl ether or mixtures of these solvents. A suitable temperature range is between −20° C. and the boiling temperature of the reaction mixture. Preferably the reduction can be carried out at room temperature.

The amides of Formula VIII can be obtained by reacting amino-protected ω-aminocarboxylic acids of the general Formula IX,

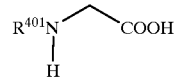

wherein $R^{401}$ has the above meaning, with the amines of the general Formula X,

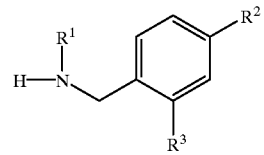

wherein $R^1$, $R^2$ and $R^3$ have the above meanings, using conventional methods for the formation of amide groups by aminoacylation. The acids of Formula IX or their reactive derivatives can be used as acylation agents. In particular, mixed acid anhydrides and acid chlorides or acid bromides of the acids of Formula IX or mixed esters of the acids of Formula IX with chloroformic acid or with organic sulfonic acids, for example aromatic sulfonic acids, such as benzenesulfonic acids substituted by lower alkyl or halogen, e.g. p-toluenesulfonic acid, are suitable as reactive derivatives. The acylation can be effected in an organic solvent which is inert under the reaction conditions, at temperatures between −20° C. and room temperature, preferably at room temperature. Suitable solvents include aromatic hydrocarbons such as benzene or toluene, aliphatic ethers such as diethyl ether, THF or dioxane, partially halogenated lower hydrocarbons such as dichloromethane or mixtures of these solvents.

The acylation can advantageously be carried out in the presence of an acid-binding reagent, particularly if an acid halide of the acids of Formula IX is used as acylation agent. Suitable acid-binding reagents include the non-nucleophilic organic bases given above for the reaction of the carbamoyl compounds of Formula IV with the compounds of Formula V.

If the acids of Formula IX themselves are used as acylation agents, the reaction of the amines of Formula X with the acids of Formula IX can advantageously also be carried out in the presence of a coupling reagent known from peptide chemistry to be suitable for amide formation. Examples of coupling reagents which promote the amide formation with the free acids by reacting with the acid in situ, forming a reactive acid derivative, include in particular: alkyl carbodiimides, e.g cycloalkyl carbodiimides such as dicyclohexyl carbodiimide or 1-ethyl-3-[(dimethylamino)-propyl]-carbodiimide, diisopropyl carbodiimide and carbonyl diimidazole. The reaction in the presence of a coupling reagent can advantageously be performed at temperatures between −30° C. and +50° C. in solvents such as halogenated hydrocarbons and/or aromatic solvents such as optionally substituted benzenes, and optionally in the presence of an acid-binding organic compound, for example a non-nucleophilic nitrogen base as described above. The acids of Formula IX represent amino-protected derivatives of 2-aminoacetic acid derivatives, which are known in the unprotected form and which can be converted into the amino-protected derivatives using known methods.

The compounds of Formula X are known, or may be prepared from known compounds in known manner.

The compounds of Formula I and their acid addition salts have properties which are antagonistic to neurokinin (=NK) receptors and are suitable for the treatment of pathological conditions in which neurokinins are involved as transfer agents. In this case, the group of compounds according to the invention is distinguished by a particularly beneficial selective activity profile which is characterized by a high affinity to NK-1 receptors with a lesser affinity to NK-2 receptors relative thereto. Furthermore, the compounds have good oral effectiveness.

Due to its activity profile, the group of substances according to the invention is suitable in particular for inhibiting processes in which neurokinins, such as substance P, which bind to NK-1 receptors, are involved. Thus the substances are selectively suitable for the treatment of conditions in which substance P is involved. Substance P plays a part, for example, in the transmission of pain, emesis, neurogenic inflammations, bladder inflammation, inflammatory joint diseases and asthmatic complaints. Due to the action which is advantageously directed at the gastrointestinal tract, the activity profile of the substances is suitable for the treatment of functional and inflammatory disturbances in the gastrointestinal tract. Furthermore, it is generally accepted that compounds which in addition to a high affinity to NK-1 receptors also have a certain affinity to NK-2 receptors, have a beneficial synergistic influence on mechanisms which are involved in the same clinical picture. The functional disturbances which can be treated by the compounds according to the invention include in particular the disturbances of the lower intestinal tracts known as so-called "irritable bowel syndrome" (=IBS). The essential symptoms of IBS are pains in the lower abdomen, which appear to be due to hypersensitivity of the visceral afferent nervous system, and anomalies in bowel movement, in particular abnormally accelerated passage of the stool in the colon. The increased visceral sensitivity to pain with respect to mechanical or chemical irritants in the intestinal tract results in IBS patients suffering severe visceral pains even upon only physiological slight distension of the colon owing to digestion, e.g. even upon slight gas formation and slight flatulence, which are scarcely noticed by healthy individuals. Inflammatory disturbances in the gastrointestinal tract which can be favorably influenced by the compounds according to the invention include the inflammatory disturbances in the small intestine and large intestine regions generally grouped under the term IBD (=inflammatory bowel disease), including ulcerative colitis and Crohn's disease. The activity profile of the substances is distinguished by good oral bioavailability with beneficial selectivity of the activities antagonistic to neurokinin receptors with respect to unwanted side-effects. Thus, in dose ranges which block the NK-1 receptor, in pharmacological tests no cardiovascular calcium-antagonistic action was detected.

The example numbers mentioned below refer to the following preparative examples.

Description of the pharmacological test methods
1. Determination of the binding power of the test substances to NK-1 receptors in vitro.

The affinity of the test substances to human NK-1 receptors was measured in vitro. The inhibition of the binding of the physiological neurokinin (substance P) to neurokinin-1 receptors was determined.

The receptor binding studies were performed with [$^3$H]-substance P as ligand. For the binding test, different samples of a membrane preparation of CHO cells (=egg cells of the Chinese hamster, Chinese hamster oocytes), which express the human NK-1 receptor, were incubated with a solution of the labeled ligand, with the incubation mixtures containing no test substance or additions of different concentrations of test substance. Then, bound and free ligands in each of the samples were separated with the aid of glass-fibre filtration. The fraction remaining in the filter was washed several times with buffer solution, and then the radioactivity of the fraction remaining in the filter was measured using a beta scintillation counter. That concentration which effects half maximum displacement of the bound ligand was determined as $IC_{50}$ of the respective test substance. From this, the corresponding inhibition constant ($K_i$ value) of the test substance was calculated. In this test model, the substance of Example 1 showed a $K_i$ value of 2.1 nmole/l for the affinity to human NK-1 receptors.

2. Determination of the binding power of the test substances to NK-2 receptors in vitro.

The affinity of the test substances to human NK-2 receptors was measured in vitro. The inhibition of the binding of the compound SR-48,968 to NK-2 receptors was determined. SR-48,968 is a synthetically-produced compound known to be a specific NK-2 antagonist.

The receptor binding studies were performed with SR-48,968 as ligand. The test was performed corresponding to the method given in the pharmacological test for determining the binding power of the test substances to NK-1 receptors in vitro. In contrast to this, then, however, various samples of a membrane preparation of CHO cells which express the human NK-2 receptor were used. In this test model, the example substances listed in Table 1 below showed the given $K_i$ values for the affinity to human NK-2 receptors:

TABLE 1

| Affinity of the test substances to human NK-2 receptors | |
|---|---|
| Example No. | $K_i$ [µmole/l] |
| 1 | 0.06 |
| 2 | 0.05 |
| 3 | 0.30 |

3. Determination of the functional NK-1 antagonism of the test substances on isolated tissue of guinea pigs in vitro The antagonistic activity to NK-1 receptors of the test substances was measured in vitro on isolated ring preparations, kept in an oxygenated nutrient solution, of the aortas of Pirbright-White guinea pigs. The inhibition by the test substances of the relaxation of tone of the aorta preparations, caused after stimulation with the NK-1 agonist substance P, was determined.

In order to measure the contraction of the vessel muscles, the preparations were fixed to a hook, joined by a thread to a force measuring apparatus and the contractions were recorded in each case on a plotter. The aorta preparations were tonicised with phenylephrine. Then before and after the administration of the test substance the NK-1 receptors of the preparations were stimulated with 0.01 μmole substance P, which caused relaxation of the tone. The relaxations before and after the administration of the test substance were quantified in percent. As a parameter, the concentration of the half maximum inhibition (=$IC_{50}$) was calculated, which indicates the concentration for which a half maximum inhibition of the relaxation of the tone occurs.

In this test model, the example substances listed in Table 2 below showed the given $IC_{50}$ values for the half maximum inhibition:

TABLE 2

Functional NK-1 antagonism of the test substances on isolated guinea-pig tissue.

| Example No. | $IC_{50}$ [μmole/l] |
|---|---|
| 1 | 0.001 |
| 2 | 0.0012 |
| 3 | 0.0015 |

4. Determination of the substance-P-antagonistic action of the test substances in vivo.

In order to demonstrate the substance-P-antagonistic activity of the test substances, the hypotension caused by administration of substance P in guinea pigs was used as the standard test model for substance P-induced pharmacological effects. The inhibiting effect of the test substances was determined with respect to vasodepression induced by substance P after intravenous (=i.v.) and intraduodenal (=i.d.) administration of the test substances.

Male guinea pigs each had a catheter implanted in a common carotid artery and a jugular vein under anaesthesia (ketamine 67 mg/kg, xylazine 13 mg/kg). The arterial catheter served to measure the blood pressure. Measurement was effected using a Statham 23d/B pressure gauge. The administration of substance P and, in the case of intravenous administration, also the administration of the test substance, was effected by means of the venous access. After a 20-minute equilibration phase, 50 pmole/animal of substance P were administered i.v. as a bolus. Then the test substance was administered. For the i.v. investigation, the test substance was administered intravenously in metered doses of 0.1, 0.46 or 1.0 μmole/kg to a group of 4 to 6 animals in each case. The control group was given the corresponding amount of a physiological sodium chloride solution. 50 pmole substance P were administered i.v. in each case 1, 15, 30, 45 and 60 minutes after administration of the substance. For the tests with intraduodenal substance administration, in a departure from the above description additionally a catheter was implanted in the duodenum of the test animals. The test substances were administered to 3 to 6 animals each time in metered doses of 0.046, 0.1, 0.46, 1.0, 4.6 and 10.0 μmole/kg via this catheter. Tylose was used as the vehicle for these tests. The mean arterial blood pressure was measured before and approximately 1 minute after the first administration of substance P (before administration of the test substance) and the maximum substance P-induced vasodepression was determined therefrom. After 60 minutes, the mean arterial blood pressure values of the control animals treated only with substance P and the animals treated with substance P and test substance were compared, and the inhibition of the substance P-induced vasodepression caused by the respective test substance dose was calculated in percent, relative to the maximum vasodepression, from the difference. The dose at which 50% inhibition of the substance P-induced vasodepression occurs was determined as $ED_{50}$.

In this test model, the substance of Example 1 showed an $ED_{50}$ of 0.2 μmole/kg after i.v. administration and an $ED_{50}$ of 0.08 μmole/kg after i.d. administration. This relationship of i.d. to i.v. effectiveness can be assessed as an indication that the substance is well suited for oral administration and that its action preferentially begins in the gastrointestinal tract.

In the same test model, the test substances were also investigated for hypotensive actions based on calcium-antagonistic properties. To this end, groups of control animals were administered only the test substance doses without administration of substance P. The substance of Example 1 showed no significant vasodepression in the dose range investigated (i.v. doses of up to 1 μmole/kg and i.d. doses of up to 10 μmole/kg). This is an indication that no calcium-antagonistic side-effects occurred in this dose range. The surprisingly low calcium-antagonistic side-effects of the compounds according to the invention can also be demonstrated by in vitro standard test models, for example on isolated aorta tissue of guinea pigs.

The substances may be administered in conventional pharmaceutical preparations. The doses to be used may vary individually and will naturally vary according to the type of condition to be treated and the substance used. In general, however, medicinal forms with an active substance content of 0.1 to 80 mg, in particular 1 to 10 mg, active substance per individual dose are suitable for administration to humans and larger mammals.

The compounds may be contained according to the invention, together with conventional pharmaceutical adjuvants and/or carriers, in solid or liquid pharmaceutical preparations. Examples of solid preparations include preparations which can be administered orally, such as tablets, coated tablets, capsules, powders or granules, and alternatively suppositories. These preparations may contain conventional pharmaceutical inorganic and/or organic carriers, e.g. talcum, lactose or starch, in addition to conventional pharmaceutical adjuvants, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical adjuvants and/or carriers in known manner. To produce solid medicament forms, the active substances may, for example, be mixed with the adjuvants and/or carriers in conventional manner and may be wet or dry granulated. The granules or powder may be poured directly into capsules or be pressed into tablet cores in conventional manner. These may be coated in known manner if desired.

The following examples are intended to illustrate the invention in greater detail without restricting its scope.

EXAMPLE 1

(2R)-1-[3,5-bis (trifluoromethyl)benzoyl]-2-(1H-indol-3-ylmethyl)-4-{2-[N-(2-methoxybenzyl)aminoethyl]-aminocarbonyl}piperazine.

A) 101.5 g tert. butoxycarbonylglycine were dissolved in 800 ml dichloromethane under a nitrogen atmosphere and 96.5 ml triethylamine were added thereto. 58 ml ethyl chloroformate were added slowly dropwise with ice cooling, the resulting mixture was stirred for a further 2 hours at room temperature, and then a solution of 79.8 g 2-methoxybenzylamine in 400 ml dichloromethane was added dropwise. Stirring was carried out overnight, then 1,400 ml of a 15% aqueous tartaric acid solution were added and stirring was continued for another 30 minutes. Then the organic phase was separated, dried over sodium sulfate and evaporated at reduced pressure. The remaining residue was crystallised from diethyl ether/dichloromethane and dried in a high vacuum. 88.9 g N-BOC-C-(2-methoxy)-benzylaminoglycine were obtained as a white powder, melting point=97°–97.7° C.

B) 40.0 g of the product obtained above were dissolved under a nitrogen atmosphere in 600 ml of a mixture of toluene and THF (1:1) and added dropwise to an ice-cooled receiving solution of 21.0 g LiAlH$_4$ in 500 ml THF. The mixture was stirred overnight at room temperature, and then in sequence a mixture of 20 ml water and 150 ml THF were added dropwise with ice cooling and then at room temperature first 20 ml of a 15% aqueous sodium hydroxide solution, followed by 60 ml water. The supernatant solution was drawn off from the resulting precipitate by suction and the filtrate was evaporated at reduced pressure. The residue was taken up in 240 ml of a 7.5% aqueous tartaric acid solution and the aqueous phase was extracted with dichloromethane. Then the aqueous phase was brought to pH 10 by the addition of 200 ml of a 10% aqueous sodium hydroxide solution and was extracted three times more with dichloromethane. The combined dichloromethane phases were dried over sodium sulfate, evaporated at reduced pressure and dried in a high vacuum. 28.0 g oily N-BOC-N'-(2-methoxy)benzyl-1,2-diaminoethane were obtained, which was reacted further without purification.

C) 5.0 g of the product obtained above were dissolved in 50 ml THF under a nitrogen atmosphere. 20 ml of a 1N aqueous sodium hydroxide solution were added thereto. With ice cooling, a total of 3.05 g benzyl chloroformate and a 1N aqueous sodium hydroxide solution were added dropwise to the resulting reaction mixture simultaneously such that the pH value did not drop below 10. Once addition had been completed, stirring was carried out overnight at room temperature. Then 150 ml methyl tert. butyl ether were added, the aqueous phase was separated and the organic phase was washed in sequence with two times 50 ml water, once 50 ml of a 15% aqueous tartaric acid solution and once again two times 50 ml water. The organic phase was then dried over sodium sulfate, evaporated at reduced pressure and dried in a high vacuum. 4.9 g N-BOC-N'-(2-methoxy) benzyl-N'-Cbo-1,2-diaminoethane were obtained, which was reacted further without purification.

D) 4.8 g of the product obtained above were dissolved in 50 ml dichloromethane. 4.4 g p-toluenesulfonic acid were added thereto and the reaction mixture was stirred overnight. Then a solution of 7.5 g NaOH in 75 ml water was added. The organic phase was separated, washed once with 75 ml water, and dried over sodium sulfate. The solvent was evaporated at reduced pressure and the product was dried in a high vacuum. 3.5 g oily N-(2-methoxy)benzyl-N-Cbo-1,2-diaminoethane were obtained, which was reacted further without purification.

E) 2.0 g (2R)-1-[3,5-bis(trifluoromethyl)benzoyl]-2-(1H-indol-3-ylmethyl)-piperazine were dissolved in 100 ml dichloromethane. In succession, 0.6 g triphosgene, dissolved in 20 ml dichloromethane, and 12.0 ml diisopropylethylamine, dissolved in 20 ml dichloromethane, were added thereto. The resulting reaction mixture was stirred for 1 hour at room temperature, and then 2.8 g of the amino compound obtained above, dissolved in 20 ml dichloromethane, were added dropwise thereto. The reaction mixture was stirred for another 18 hours and then was washed in succession with 10% aqueous potassium hydrogensulfate solution, water and again with saturated sodium hydrogencarbonate solution. Then the dichloromethane phase was dried over sodium sulfate and evaporated at reduced pressure. Chromatography of the residue on silica gel (mobile solvent: dichloromethane/methanol 3:1) provided 2.5 g oily (2R)-1-[3,5-bis(trifluoromethyl) benzoyl]-2-(1H-indol-3-ylmethyl)-4-{2-[N-(2-methoxybenzyl)-N-Cbo-aminoethyl]aminocarbonyl}-piperazine, which was reacted further without purification.

F) 2.5 g of the product obtained above were dissolved in 400 ml ethanol and 0.5 g 10% palladium catalyst on activated carbon were added thereto. Then hydrogenation was carried out for 6 hours at a hydrogen pressure of 4 bar. The solution was filtered off from the catalyst, and the solvent was evaporated at reduced pressure. Chromatography on silica gel (mobile solvent: dichloromethane/methanol 9:1) provided 1.0 g crude title compound, which was converted into the hydrochloride by treatment with HCl-saturated diethyl ether, melting point=138° to 140° C.

The compounds of Formula I listed in the following Table 3 can also be prepared according to the methods described above:

TABLE 3

Further compounds of Formula I.

| Example No. | R$^1$ | R$^2$ | R$^3$ |
|---|---|---|---|
| 2 | CH$_3$ | H | OCH$_3$ |
| 3 | H | F | H |

EXAMPLE I: Tablets containing (2R) -1-[3,5-bis(trifluoromethyl)benzoyl]-2-(1H-indol-3-ylmethyl)-4-{2-[N-(2-methoxybenzyl)aminoethyl]-aminocarbonyl}piperazine.

Tablets with the following composition per tablet were produced:

| | |
|---|---|
| (2R)-1-[3,5-bis(trifluoromethyl)benzoyl]-2-(1H-indol-3-ylmethyl)-4-{2-[N-(2-methoxy-benzyl)aminoethyl]-aminocarbonyl}piperazine hydrochloride | 20 mg |
| Corn starch | 60 mg |
| Lactose | 135 mg |
| Gelatine (as 10% solution) | 6 mg |

The active substance, the corn starch and the lactose were thickened with the 10% gelatine solution. The paste was ground and the resulting granules were placed on a suitable tray and dried at 45° C. The dried granules were passed through a crusher and mixed in a mixer with the following additional adjuvants:

| | |
|---|---|
| Talcum | 5 mg |
| Magnesium stearate | 5 mg |
| Corn starch | 9 mg | and then pressed into 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be constructed broadly to include all variations falling within the scope of the appended claims and equivalents thereof.

What is claimed is:

1. A compound corresponding to the formula:

[Structure]

wherein $R^1$ is hydrogen or lower alkyl, $R^2$ is hydrogen or halogen and $R^3$ is hydrogen or lower alkoxy, or a physiologically acceptable acid addition salt thereof.

2. A compound according to claim 1, wherein said compound is (2R)-1-[3,5-bis(trifluoromethyl)benzoyl]-2-(1H-indol-3-ylmethyl)-4-{2-[N-(2-methoxybenzyl)aminoethyl]-aminocarbonyl}piperazine or a physiologically acceptable acid addition salt thereof.

3. A pharmaceutical composition comprising a pharmacologically effective quantity of a compound according to claim 1 and at least one pharmaceutical carrier or adjuvant.

4. A process for preparing a compound corresponding to the formula:

[Structure]

wherein $R^1$ is hydrogen or lower alkyl, $R^2$ is hydrogen or halogen and $R^3$ is hydrogen or lower alkoxy, or a physiologically acceptable acid addition salt thereof, said process comprising the steps of:

a) reacting a compound of Formula II

[Structure]

with a reactive carbonyl compound of formula III

[Structure]

wherein Y represents a leaving group which can be displaced by nucleophilic attack of a primary or secondary amine, to form a carbamoyl compound of formula IV

[Structure]

wherein Y has the above meaning, and then reacting the compound of Formula IV with a compound of formula V

[Structure]

wherein $R^{101}$ represents lower alkyl or an amino protective group, and $R^2$ and $R^3$ have the above meanings, and then cleaving off any protective group $R^{101}$, or b) reacting a compound of Formula II with a compound of formula VI

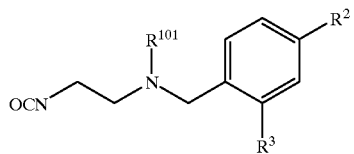

wherein $R^{101}$, $R^2$ and $R^3$ have the above meanings, and cleaving off any amino protective group $R^{101}$, and optionally alkylating a resulting compound of Formula I wherein $R^1$ is hydrogen to form a compound of Formula I wherein $R^1$ is lower alkyl, or optionally converting a resulting compound of Formula I into a corresponding acid addition salt, or optionally converting an acid addition salt into a corresponding free compound of Formula I.

5. A process according to claim 4, further comprising adding a non-aucleophilic organic base to the compound of Formula IV before reacting the compound of Formula IV with the compound of Formula V.

* * * * *